United States Patent [19]

Clark

[11] Patent Number: 4,619,609

[45] Date of Patent: Oct. 28, 1986

[54] APPARATUS FOR THE ORTHODONTIC TREATMENT OF TEETH

[76] Inventor: William J. Clark, Lundin Lea, Leven Road, Lundin Links, Fife, KY8 6AJ, Scotland

[21] Appl. No.: 684,902

[22] Filed: Dec. 21, 1984

Related U.S. Application Data

[62] Division of Ser. No. 487,929, Apr. 22, 1983, abandoned.

[51] Int. Cl.$^4$ ............................................. A61C 7/00
[52] U.S. Cl. .................................................... 433/6
[58] Field of Search ............... 433/5, 6, 19, 7, 179, 433/184, 197

[56] References Cited

U.S. PATENT DOCUMENTS

| | | | |
|---|---|---|---|
| 2,473,515 | 6/1949 | Egger | 433/169 |
| 2,479,780 | 8/1949 | Remensnyder | 433/6 |
| 2,708,314 | 5/1955 | Schwartz | 433/197 |
| 3,043,005 | 7/1962 | Morris | 433/179 |
| 3,820,242 | 6/1974 | Haskins | 433/18 |
| 4,439,149 | 3/1984 | Devincenzo | 433/6 |

*Primary Examiner*—Robert Peshock
*Attorney, Agent, or Firm*—Mason, Fenwick & Lawrence

[57] ABSTRACT

The invention is apparatus for the orthodontic treatment of teeth for the correction of malocclusion. The apparatus combines a traction system consisting of a face bow provided with a labial hook (14) whereby an elastic traction member (20) can be attached to an attachment means in the form of a hook (19) provided on the other of two dental arches. The face bow has an outer bow (11) to which elastic traction members (13) can be connected to a headcap or the like. The invention also incorporates at last two cooperating angled bite blocks (17,21), said bite blocks being located in upper and lower dental arches respectively. The bite blocks (17,21) act to promote mandibular displacement between the upper and lower dental arches.

4 Claims, 8 Drawing Figures

APPARATUS FOR THE ORTHODONTIC TREATMENT OF TEETH

This is a division of application Ser. No. 487,929, filed Apr. 22, 1983, and now abandoned.

This invention relates to apparatus for the orthodontic treatment of teeth, particularly but not exclusively for the correction of malocclusion.

It has been previously proposed to treat malocclusion by the provision of face bows. Face bows are generally made of stainless steel spring wire and consist of an inner bow which is attachable to an appliance in the mouth of a patient and an outer bow integrally attached to the inner bow substantially at their mid points. The outer bow terminates in a hook at each end and is adapted to be positioned outside the cheeks of a patient so that elastic traction can be attached to the end hooks and connected to a headcap or neckstrap worn by the patient.

Such previously proposed face bows are effective to a limited extent but in many cases combined extra-oral and inter-maxillary traction is desirable.

An object of the present invention is to provide improved apparatus for the orthodontic treatment of teeth which will enable an achievement of inter-maxillary and or extra-oral traction to the maxillary and mandibular teeth in the treatment of teeth for the correction of malocclusion.

According to the present invention there is provided apparatus for the orthodontic treatment of teeth for the correction of malocclusion comprising a face bow for attachment to one of the upper or lower dental arches of a patient, said face bow comprising an inner bow for attachment to the dental arch, an outer bow adapted when in use to be located externally of the patient for the application of traction thereto, and forwardly projecting first attachment means to enable the application of additional traction between said attachment means and the other of said upper and lower dental arches thereby effecting inter-maxillary traction.

According to another aspect of the present invention there is provided apparatus for the orthodontic treatment of malocclusion comprising at least two cooperating bite blocks adapted to be attached to upper and lower dental arches, said upper and lower bite blocks having cooperating pressure surfaces thereon and adapted when in use, to assist in achieving a predetermined positional relationship between the upper and lower dental arches.

Embodiments of the present invention will now be described by way of example with reference to the accompanying drawings, in which.

Figure 4A:
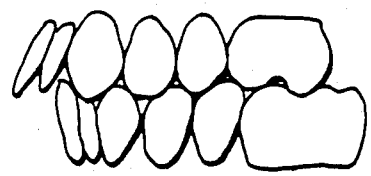
Figure 4B:
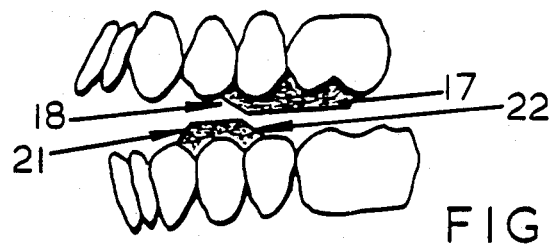
Figure 4C:
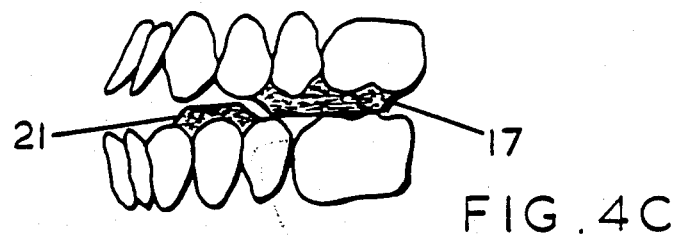
Figure 5:
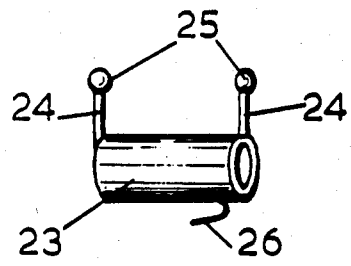
Figure 6:
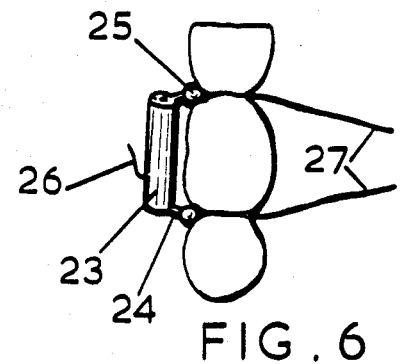

FIGS. 4A, 4B, and 4C illustrate progressive mandibular displacement arising from the use of complementary bite blocks in accordance with the invention;

FIG. 5 is a side view illustrating a face bow fixing element for enabling a face bow to be attached to teeth; and FIG. 6 is a plan view of the fixing element of FIG. 5 showing it in position in relation to teeth.

Figure 1:
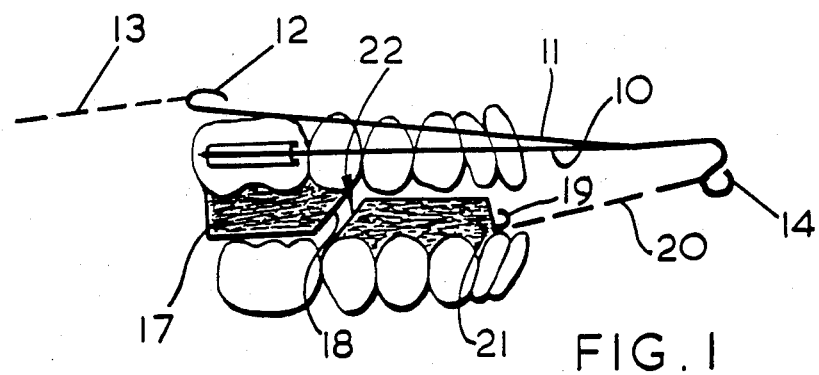
FIG. 1 is a diagrammatic side view of apparatus for the orthodontic treatment of teeth in accordance with the present invention.
Figure 2:
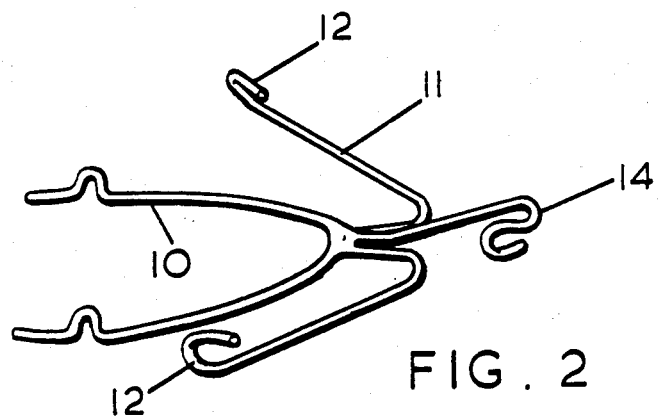
FIG. 2 is a perspective view of a face bow utilized in the present invention.
Figure 3:
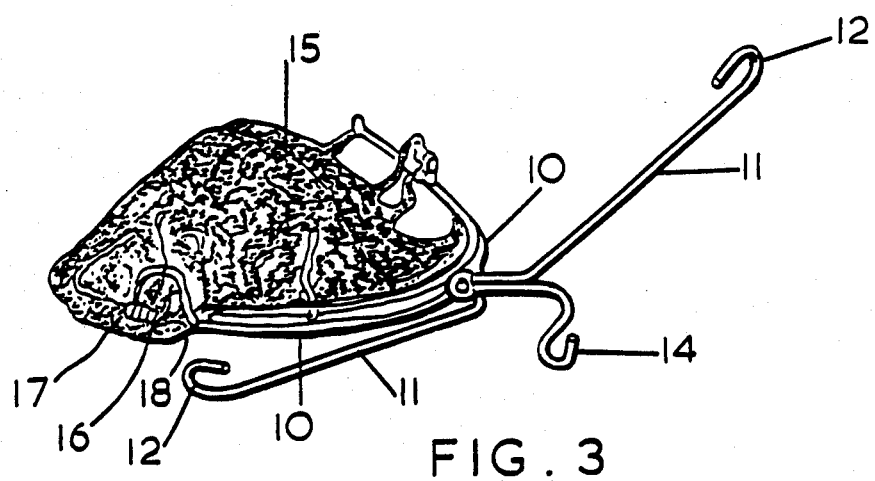
FIG. 3 is a perspective view of a face bow of the invention when fitted to an appliance in the form of a palatal plate.

Referring to the drawings, apparatus for orthodontic treatment of malocclusion comprises a face bow as illustrated in FIG. 2, said face bow having an inner bow 10 for attachment to the upper dental arch of a patient. An outer bow 11 is integrally secured to the inner bow 10 adjacent their respective mid points and the outer bow 11 is adapted to extend outside the cheeks of the patient and is provided with hooks 12 at each end for the attachment of an elastic traction member 13 to a headcap or neckstrap (not shown) worn by the patient. Integrally secured to the junction of the inner and outer bows 10 and 11 at the mid-line thereof is a forwardly projecting labial hook 14.

The means for enabling attachment of the inner bow 10 of the face bow to the upper dental arch comprises a moulded palate plate 15 of suitable synthetic plastics material having wire retainers 16 molded thereinto for attachment of the plate to the upper teeth and for receiving and retaining the free ends of the inner bow 10 to retain the bow in position. As an alternative to the wire retainers 16, fastening devices such as tubular fastening devices described hereinafter with reference to FIGS. 5 and 6 can be employed. An arch wire (not shown) can also be moulded into the plate 15 if desired.

The synthetic plastics palate plate 15 incorporates a wedge or bite block 17 at each posterior side, each bite block 17 having a downwardly and rearwardly angled pressure surface 18. Each block 17 is positioned so that in use it is located over the occlusal surfaces of the upper buccal teeth.

The lower dental arch is also provided with a synthetic plastic moulding (not shown) similar to the palate plate 15 of the upper dental arch, the lower plastic moulding conforming to the inner profile of the teeth of the central lower dental arch. The lower moulding has spring fixing wires or clasps moulded into it for attachment to the mandibular teeth as well as a rearwardly directed wire hook 19 located centrally of the lower dental arch for attachment of an elastic traction member 20. The lower moulding is also provided with integral posterior wedges or bite blocks 21 which, when the moulding is fitted, are located over the occlusal surfaces of the lower buccal teeth and each block 21 has an upwardly and forwardly angled pressure surface 22 which cooperates with the angled pressure surface 18 of one of the cooperating upper blocks of the upper palatal plate 15. The cooperating angled pressure surfaces 18 and 22 of the upper and lower blocks 17 and 21 respectively are disposed at approximately 45° when in use.

As can be seen from FIG. 4, FIG. 4A illustrates a condition of a patient in which the teeth of the upper jaw protrude relative to the teeth of the lower jaw. FIG. 4B illustrates the same teeth as in FIG. 4A but to which upper and lower bite blocks 17 and 21 have been fitted. FIG. 4B shows the position where the teeth of the upper and lower jaw are about to be closed in order to bring the pressure surfaces 18 and 22 into engagement with each other. FIG. 4C illustrates the position in which the teeth of the upper and lower jaw have been closed one upon the other to cause the pressure surfaces 18 and 22 to engage one another and to cause relative functional mandibular misplacement of the upper and lower teeth, i.e. the upper teeth and jaw tend to be moved rearwardly and the lower teeth and jaw tend to be moved forwardly. By location of the bite blocks 17 and 21 over the occlusal surfaces of the buccal teeth, the tongue space is not restricted and downward and forward mandibular growth is prompted.

In use of the apparatus for the correction of dental arch relationship in Class II malocclusion, the upper plate 15 and lower moulding are attached by clasps or the like to the upper and lower teeth respectively, so that on biting, the cooperating angled surfaces 18 and 22 of the upper and lower blocks 17 and 21 respectively tend to cause a forward mandibular displacement as described above. The free ends of the inner bow 10 of the face bow are then fitted to the spring wire retainers 16 carried by the upper palatal plate 15 so that the labial hook 14 extends forwardly. Elastic traction members 13 are then connected between end hooks 12 of the outer bow 11 and headcap or neckstrap and a generally horizontally extending traction member 20 is also connected between the labial hook 14 on the face bow and the rearwardly directed attachment hook 19 on the lower moulding. Such elastic traction tends also to effect inter-maxillary traction in order to promote forward mandibular displacement.

It will be readily apparent that modifications can be made to the embodiment describe above without departing from the scope of the invention. For example, the face bow can be fitted to the palatal plate 15 by means other than spring wire retainers. For example, the face bow can be integrally moulded into the palatal plate. In a further alternative embodiment, the face bow as described in FIG. 2 can be retained by tubular fixing members as illustrated in FIGS. 5 and 6 as described hereinafter. In a further form of the invention, the bite blocks 17 and 21 need not be formed as part of an upper or lower palatal moulding but can be formed merely as blocks to which the tubular retainers of FIGS. 5 and 6 are integrally formed. The preformed blocks can then be directly bonded to the upper and lower teeth.

FIGS. 5 and 6 show a preformed fixing element for a face bow consisting of a tube 23 of any suitable material such as stainless steel. The tube 23 has connected thereto at adjacent each of its ends a clasp constituted by a spring leg 24 terminating in a ball 25. The legs 24 form a clasp which enables the tube to be releasably engaged with undercuts in the inter-dental areas. If desired, the tube 23 can be provided with an integral hook 26 whereby traction can be applied, for example to other teeth, through the intermediary of an elastic traction member. As shown in FIG. 6, the tube 23 is provided with a pair of wire tags 27 by means of which the tube 23 can be connected to an appliance such as a palatal plate or a bite block, the wire tags extending over inter-dental embrasures in order to secure the fixing element to the appliance.

The fixing element consisting of tube 23 and clasp formed by legs 24 can be made of any suitable dimensions to fit on a single molar or pre-molar teeth or on two adjacent teeth.

From the above it will be understood by those skilled in the art that the traction forces described provide inter-maxillary and extra-oral traction to the maxillary and mandibular teeth in order to correct the relationship between upper and lower dental arches.

The traction system of the present invention combines extra-oral traction with an improved method of applying inter-maxillary traction which overcomes unfavourable components of force associated with conventional methods of inter-maxillary traction. The point of application of traction force in the lower arch is not limited to the anchor molars and the direction of the inter-maxillary force can be controlled.

It will be appreciated that the elastic traction mechanism can be used independently of the wedge blocks and similarly the wedge blocks can be used independently of the elastic traction mechanism. It is, however, considered to be much more preferable to use both the elastic traction mechanism incorporating the face bow and the bite blocks together. When used together, they complement each other in assisting in the corrective process by altering the position of occlusion of the lower dental arch relative to the upper dental arch. If the combination of the elastic traction mechanism and bite blocks is employed and a patient, for example, during night-time use, fails to posture to the corrected occlusal position dictated by the blocks, then compensation is automatically provided by an increase in the intermaxillary traction force applied by the elastic traction system.

If desired, wedge bite blocks having oppositely directed pressure surfaces to those described in the foregoing embodiments can be employed for the treatment of selected Class III malocclusions.

It has been found that by using the elastic traction system in combination with the cooperating wedge bite blocks, rapid correction of arch relationship in Class II malocclusion can be achieved. For example, full anteroposterior correction of arch relationships has been effected in three to six months and improved facial balance indicates rapid skeletal adaptation in severe Class II skeletal malocclusions. The technique of the present invention combines features normally associated with separate disciplines of fixed, functional and removable appliance techniques. The uncertainties of individual response sometimes associated with full-time functional or mechanical techniques are obviated or mitigated by the apparatus of the invention by combining a full-time functional technique with an elastic traction system.

I claim:
1. Apparatus for the orthodontic treatment of malocclusion of a patient whose closed upper and lower dental arches of natural teeth define an occlusal plane, said apparatus comprising:
   (a) first and second cooperating bite blocks;
   (b) means for securing said first and second bit blocks respectively to the upper and lower dental arches; and
   (c) said upper and lower bite blocks having respective cam surfaces cooperating with each other and oriented with respect to the occlusal plane to exert opposing forces upon the upper and lower dental arches, whereby the occlusion therebetween is adaptively changed.
2. Apparatus as claimed in claim 1, in which each block is provided with retaining means for enabling a face bow to be releasably located therein.
3. Apparatus as claimed in claim 2, in which said retaining mean is an integral tube.
4. Apparatus as claimed in claim 1, in which said cam surfaces of said first and second bite blocks are disposed at an angle of substantially 45° relative to a plane of the teeth in their respective dental arch.

* * * * *